United States Patent [19]

Dropps

[11] Patent Number: 5,994,880

[45] Date of Patent: Nov. 30, 1999

[54] GIANT MAGNETRORESISTIVE RATIO SENSING SYSTEM

[75] Inventor: Frank Dropps, Maple Grove, Minn.

[73] Assignee: Angeion Corporation, Brooklyn Park, Minn.

[21] Appl. No.: 09/056,321

[22] Filed: Apr. 7, 1998

[51] Int. Cl.$^6$ .......................... H01M 10/44; H01M 10/46
[52] U.S. Cl. ............................. 320/140; 320/166; 607/14
[58] Field of Search ...................... 320/128, 130, 320/132, 136, 140, 166, DIG. 28; 324/255, 256, 257, 261, 234; 607/4, 9, 14, 25, 26, 27, 29

[56] References Cited

U.S. PATENT DOCUMENTS

| | | |
|---|---|---|
| 5,709,225 | 1/1998 | Budgifvars et al. . |
| 5,722,998 | 3/1998 | Prutchi et al. . |
| 5,764,052 | 6/1998 | Renger . |
| 5,782,883 | 7/1998 | Kroll et al. ................................ 607/14 |

OTHER PUBLICATIONS

Klopper et al. A sensor for Balancing Flux in Converters with a High–Frequency Transformer Link, IEEE Transactions on Industry Applications, 33.3 pp. 774,1997.

Moskowicz. Transformer Sensor of Magnetic Field Intensity. Third International Symposium on Mehtods and Models in Automation and Robotics, Sept. 1996.

NonVolatile Electronics, Inc. Engineering and Application Notes. Internet Oct. 6, 1997.

NonVolatile Electronics, Inc. An ISO 9001 Certified Company. Internet Jan. 1998.

*Primary Examiner*—Edward H. Tso
*Attorney, Agent, or Firm*—Brad Pedersen

[57] ABSTRACT

A magnetic sensing circuit is arranged in cooperative relation to a flyback transformer in a capacitor charging circuit for directly sensing the state of the transformer magnetic field for controlling the switching of power to the primary winding of the flyback transformer. A first threshold is sensed when the flyback transformer is nearly saturated with magnetic energy storage. A second threshold is sensed when all of the magnetic energy stored in the flyback transformer has been transferred to the capacitor. The sensed thresholds are used to optimally control the switching of power to the primary winding to maximize the efficiency and minimize the charging time of the capacitor charging circuit. A capacitor charging circuit which utilizes the present invention can be part of an implantable cardioverter defibrillator.

15 Claims, 5 Drawing Sheets

GIANT MAGNETORESISTIVE RATIO SENSING SYSTEM

BACKGROUND OF THE INVENTION

1. Field of the Invention

This invention relates generally to the field of measurement of field leakage in a flyback transformer; and, more particularly, it relates to a sensing circuit utilizing a Giant Magnetoresistive Ratio (GMR) device to sense field leakage of a flyback transformer. Still more particularly, the invention relates to a sensing circuit for use in controlling the capacitor charging functions of an Implantable Cardioverter Defibrillator (ICD).

2. State of the Prior Art

Various types of circuits utilize flyback transformers to perform a DC/DC conversion that permits a step up from a source voltage to a required amplified voltage. Flyback transformers employ a primary winding, a ferromagnetic core, and one or more secondary windings. Current is driven through the primary winding by a current driving circuit so that electrical energy is transformed in the core to magnetic energy until such time as the core nears saturation. Once the core nears saturation, the current driving circuit opens the primary winding. With the primary winding opened, the primary current loses its original path. Since the energy in the magnetic field of the flyback transformer is proportional to the current squared, and since energy must be conserved in the closed system of the flyback transformer, a secondary current must appear through the secondary winding to conserve the total flyback transformer energy. The secondary current then continues to flow until the magnetic field has collapsed. In the case of a capacitor charging circuit, the secondary current flows into and charges a capacitor connected to the secondary winding, typically through a blocking diode.

Upon saturation, the primary winding appears nearly as a short circuit to the current driving circuit that is providing power to the primary winding, thus subjecting the current driving circuit to severe, damaging current carrying conditions. This also causes excess heat build-up in the flyback transformer which can cause damage to the primary winding and lower the flyback transformer charging efficiency. To avoid this damage, it has been found to be advantageous to have the current driving circuit interrupt current flow in the primary winding just prior to saturation of the core to maximize magnetic energy storage in the core while avoiding the high current carrying conditions.

With the flyback transformer approach, there are many limitations on efficiency. For example, while the use of ferromagnetic core materials result in increased energy densities, the resultant hysteresis losses occurring during switching adds to the power consumption requirements of the current driving circuits. That is, the hysteresis loss decreases the charging circuit efficiency and more energy must be applied to the flyback transformer to make up for the lost energy. This can be especially problematic for battery powered charging systems. The rate of switching can also have an effect on hysteresis losses, as well as the rate of heating that can occur in the flyback transformer. The charging circuit must accommodate these inefficiencies, which can result in excessive capacitor charging times and decreased battery lifetimes for battery powered charging systems.

One type of device that utilizes flyback transformers is the Implantable Cardioverter Defibrillator (ICD). This type of device is implanted in the body of a patient, and utilizes a charged capacitor to administer electrical pulses to the patient's heart. In general, the ICD has a battery coupled to a charging circuit that includes a flyback transformer for charging one or more capacitors interconnected in series to provide a high voltage output. By using the flyback transformer, a battery voltage, for example, on the order of about six volts DC, in a series of interrupted steps can cause the capacitor (or series of capacitors) to be charged to a level of about 750 volts DC, thereby providing a voltage level capable of providing an adequate charge to stimulate the patient's heart for the purpose of defibrillating the heart.

The prior art has recognized the desirability of limiting current in the primary winding of the core of a flyback transformer to as near to saturation as possible to maximize magnetic energy storage in the core while avoiding the problems caused by the high current flow levels in the primary charging circuit during saturation. Existing solutions have included measuring current flow to allow estimation of sufficiency of primary current flow necessary to bring the transformer core to near saturation. Since each transformer structure varies somewhat as a result of manufacturing tolerances, this approach requires having a safety margin to avoid saturation resulting in decreased efficiency. The choice of frequency of operation of the transformer may also impact the safety margin as there is a tradeoff between charging efficiency and transformer size, since high frequency switching allows small transformer sizes but increases hysteresis losses. Further, any heating of the flyback transformer also reduces efficiency, and thus impacts the safety margin. As a result, this approach to improve the efficiency of the flyback transformer by measuring primary winding current flow necessarily has lower efficiency once the safety margin is increased to accommodate the various factors discussed above.

Another prior art approach to improve the efficiency of the flyback transformer is by controlling the duration of the application of power to the primary winding of the flyback transformer. With the timed approach, various factors are considered such as the characteristics of the battery supply, the primary current driving circuit capability, the flyback transformer size and efficiency, and the switching frequency, all in order to estimate the fixed time each primary charging cycle that power should be applied to the primary winding. This approach however has many of the same problems as the above approach of measuring primary winding current. Again, as with the above approach, once the various factors are accommodated to build in a safety margin to the fixed time necessary to charge the primary winding to avoid saturation, the result is a less than optimal energy transfer.

While the above problems in the prior art relate to the optimal interruption of current flow in the primary winding just prior to saturation of the core to maximize energy transfer, yet another problem exists in the prior art regarding the optimal reapplication of power to the primary winding after it has been removed.

In the prior art, various approaches have been used to determine when to optimally reapply power. When the power applied to the primary winding is switched off for example, the voltage across the primary winding decreases as the field collapses. Once the voltage across the primary coil passes through zero, it is possible to again apply power in the primary circuit to start the next cycle of magnetic energy buildup via the primary winding. Thus one approach in the prior art has attempted to detect the zero volt crossover of the primary winding to provide activating signals to enable the primary charging circuit. This approach however is not optimal due to the high degree of difficulty in measuring the voltage transition point due to the high rate of transition of the voltage across the primary.

Other approaches have attempted to measure the voltage across the secondary winding while the magnetic energy in the collapsing magnetic field is being converted to electrical energy stored in the capacitor. With these approaches, an attempt is made to determine when the secondary current induced in the secondary winding has been discharged into the capacitor so that power may be reapplied to the primary winding. Often times these approaches are not optimal due to the difficult in measuring the secondary voltage to determine the precise time at which the secondary current is equal to zero so that the primary power may be reapplied. Approaches using a fixed time delay or fixed voltage reference are still not optimal for the reasons discussed earlier.

Yet other problems exist in the prior art with regards to ICDs. When the capacitor is discharged in a ICD, the initialization of charging requires special handling. As described above, it is common to use the voltage measured across the primary winding as a determining factor to recognize when power can be reapplied to the primary winding. Unfortunately, this voltage measurement approach is not available during the initial charging cycles of the primary winding. As the capacitor is charged, the stored voltage level across the capacitor is reflected back through the secondary winding to the primary winding. When the sequence of charging cycles first start, the reflected primary voltage swing is too small to accurately detect the zero crossing threshold. To accommodate this condition during the initial charging cycles, a predetermined time delay has been utilized. For the reasons discussed above, this approach is not optimal.

What is desired is an approach to determine when to remove and when to reapply power to the primary winding which is not subject to the inherent inefficiencies of the above approaches, and which is not affected by ambient or operating conditions or manufacturing tolerances.

SUMMARY OF THE INVENTION

The present invention provides a system which improves the efficiency of a high voltage capacitor charging circuit by optimally controlling the application and removal of power to a primary winding of the flyback transformer during the charging process. The system uses one or more magnetic sensors coupled to the magnetic field of the flyback transformer for sensing magnetic field strength. The system senses the magnetic field strength of the flyback transformer at a maximum level to optimally switch power away from the primary winding just before the flyback transformer is saturated with magnetic energy. The system senses the magnetic field strength is at a minimum level and switches power back to the primary winding to begin recharging the primary winding when the secondary winding has completely converted the magnetic energy in the collapsing magnetic field of the primary winding to stored electrical energy in the capacitor. By sensing the magnetic field at the maximum and minimum level the system maximizes efficiency of the capacitor charging circuit by optimizing the efficiency of the total energy transfer from the primary to the secondary winding and from the secondary winding to the capacitor.

The system provides magnetic field sensors which have a linear output voltage response to the magnetic field strength of the flyback transformer. The output of the magnetic field sensors couple to switching logic which switches power to and from the primary winding of the flyback transformer at the maximum and minimum magnetic field levels to maximize the overall charging efficiency of the charging circuit.

In a preferred embodiment, the present invention provides an improved control circuit for use in an Implantable Cardioverter Defibrillator (GCD) device having a capacitor for providing electrical signals to a patient, and a charging circuit for charging the capacitor, the charging circuit including a flyback transformer. In one aspect, the improved control circuit includes a magnetic field sensor coupled to the flyback transformer field for providing control signals to the charging circuit for switching the charging circuit off prior to the flyback transformer being driven to core saturation. This eliminates the need for sensing a drop of primary coil voltage or for providing controlled predetermined estimated timing of application of the charging current.

Yet another objective of the invention is to provide an improved control circuit which includes a Giant Magnetoresistive Ratio (GMR) sensor coupled to the flyback transformer field for sensing the state of the magnetic field and providing signals indicative thereof, and to provide control circuitry for reactivating the charging circuit on a predetermined sensed excursion of the magnetic field for maximizing the use of the residual magnetic energy storage within the flyback transformer core. This raises the efficiency of the charging circuit by utilizing the residual state of the core on each subsequent charge cycle.

Yet another aspect of the improved control circuit includes the use of the magnetic sensor upon initialization of charging of the capacitor to sense the magnetic field of the flyback transformer rather than attempting to sense reflected primary voltage or setting a predetermined reinitialization delay. Such direct sensing of the magnetic field allows initializing cycles to be handled in the same manner as later cycles and therefore increases the efficiency of the charging cycles.

These and other more detailed and specific purposes and objectives of the invention will become apparent from consideration of the drawings and Detailed Description of the Invention.

DETAILED DESCRIPTION OF THE INVENTION

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

Figure 1:
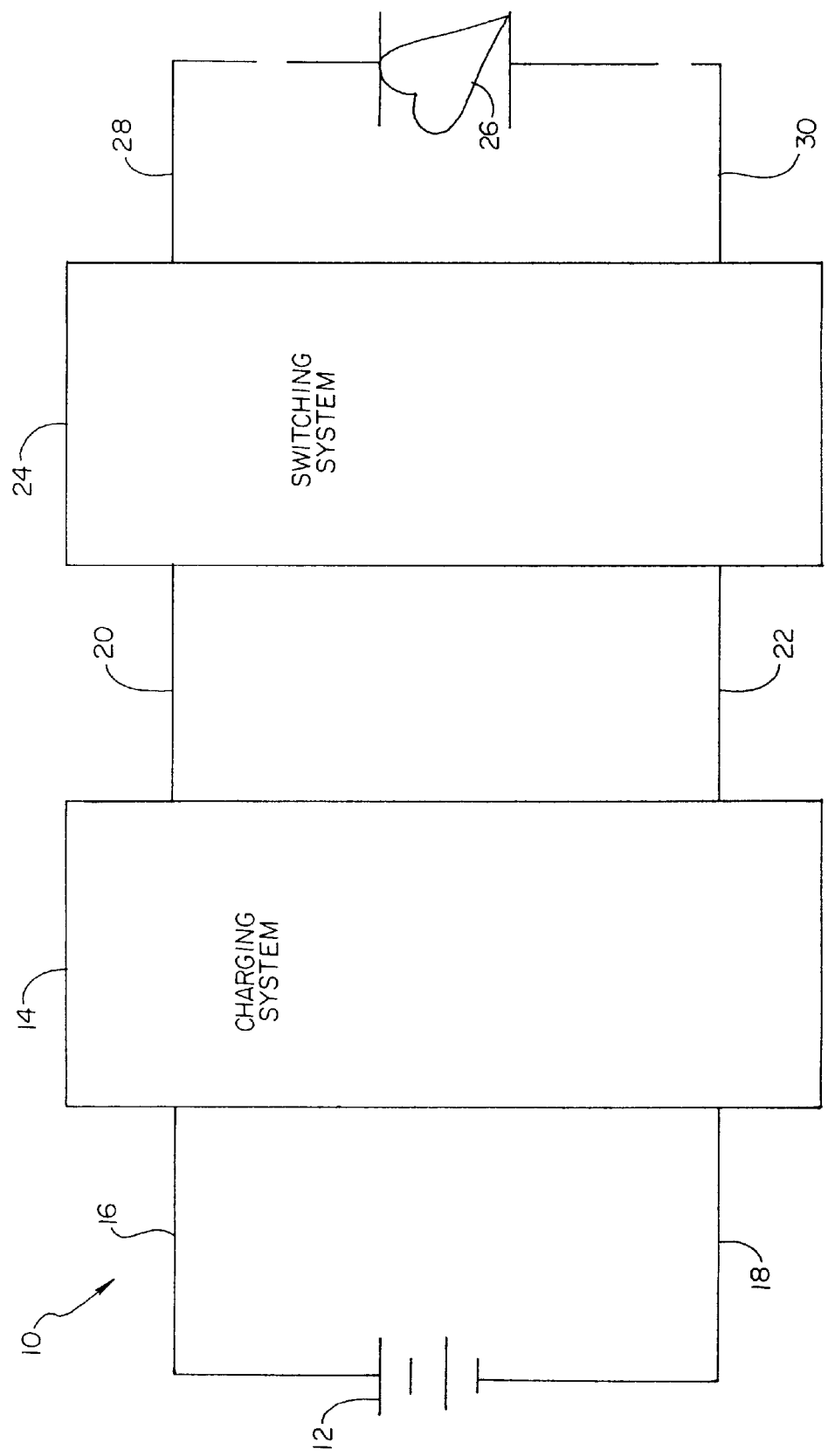
FIG. 1 is a block diagram of the preferred implantable cardioverter defibrillator system 10 in which the present invention is utilized.

FIG. 1 is a block diagram of the preferred Implantable Cardioverter Defibrillator (ICD) system 10 in which the present invention is utilized. It is understood that the present invention may be incorporated in any charging system which uses a flyback transformer.

Implantable Cardioverter Defibrillator System (ICD) 10 has a battery 12, a charging system 14 and a switching system 16. Battery 12 is coupled to charging system 14 via interface 16 and interface 18. In a preferred embodiment, the battery voltage is 1–6 volts. Charging system 14 converts the battery voltage to a much higher voltage to perform defibrillation (see also, FIG. 2). In a preferred embodiment, this voltage is typically 750 volts. Charging system 14 provides the 750 volt output between interface 20 and 22. Interface 20 and 22 are coupled to switching system 24. Switching system 24 transfers the energy at interfaces 20 and 22 to heart 26 via interface 28 and 30. Switching system 24 may use any number of approaches well known in the art to complete an energy transfer to heart 26. Switching system 24 may include for example a Schuder monophasic circuit, sequential pulse circuitry or H-bridge biphasic waveform circuitry. For a more detailed description of ICD system 10, reference is made to U.S. Pat. No. 5,405,363 and to the technical manuals for any of the commercially approved ICD systems.

Figure 2:
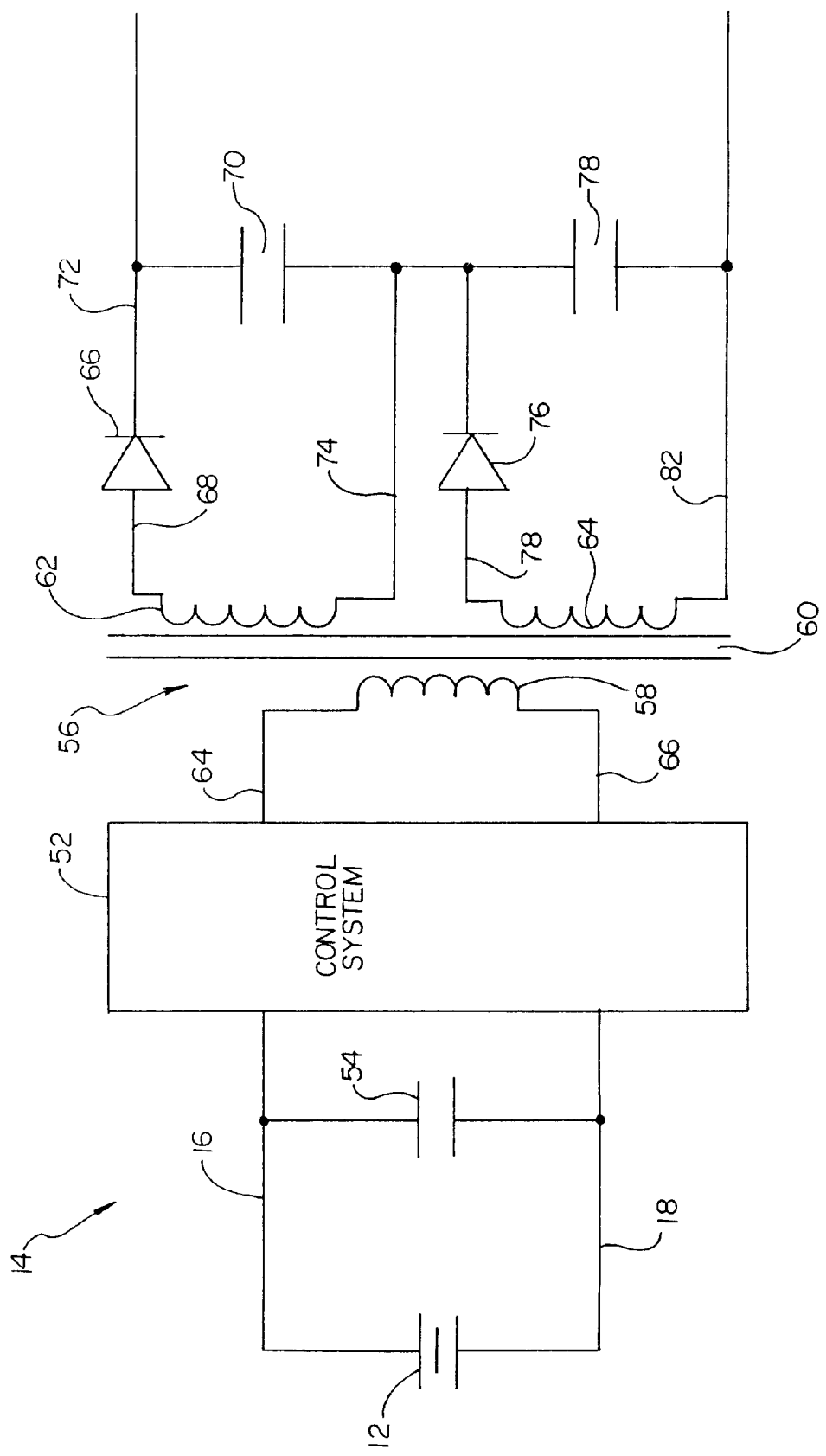
FIG. 2 is a diagram illustrating the charging system of FIG. 1.

FIG. 2 is a diagram illustrating the charging system 14 of FIG. 1 in more detail. This diagram is shown generally at 50. The positive terminal of battery 12 is coupled to control system 52 and a positive terminal of capacitor 54 via interface 16. The negative terminal of battery 12 is coupled to control system 52 and a negative terminal of capacitor 54 via interface 18. Control system 52 is coupled to primary winding 58 of flyback transformer 56 via interface 64 and 66. Control system 52 provides a switching function to couple battery 12 to primary winding 58. Capacitor 54 assists battery 12 in providing the primary current to primary winding 58 to charge flyback transformer 56 with magnetic energy. Control system 52 in combination with battery 12 and capacitor 54 provide a current driver circuit. Flyback transformer 56 also has a core 60, a secondary winding 62 and a secondary winding 64. Secondary winding 62 is coupled to diode 66 via interface 68. Diode 66 is coupled to a positive terminal of capacitor 70 via interface 72. Secondary winding 62 is coupled to a negative terminal of capacitor 70 via interface 74. As magnetic energy from primary winding 58 is transferred to secondary winding 62, secondary current flows through a forward biased diode 66 from interface 68 to interface 72 to charge capacitor 70 to a positive voltage at interface 72 with respect to interface 74. Likewise, secondary winding 64 is coupled to a diode 76 via interface 78. Diode 76 is coupled to a positive terminal of capacitor 78 via interface 74. Secondary winding 64 is coupled to a negative terminal of capacitor 78 via interface 82. Just as with secondary winding 62, secondary winding 64 provides a charging current through forward biased diode 76 from interface 78 to interface 74 to charge capacitor 78 to a positive voltage. Since the negative terminal of capacitor 70 is coupled to the positive terminal of capacitor 78, the voltage across capacitor 70 and capacitor 78 are summed to a total voltage across charging circuit outputs 72 and 82. This approach is necessary because state of the art electrolytic capacitors currently are capable only of achieving about 375 volts. Since the desired voltage output between interface 72 and interface 82 is 750 volts, capacitors 70 and 78 must be connected in series.

Charging system 14 begins charging primary winding 58 once control system 52 closes to couple interface 16 to interface 64 and to couple interface 18 to interface 66 so primary winding 56 may be charged. The primary winding current increases approximately linearly with time as flyback transformer 56 is charged with magnetic energy. At the point where flyback transformer 56 is nearly saturated with magnetic energy, control system 52 opens the connection between interface 18 and interface 66. Once this connection is open, the primary current through primary winding 58 loses its original path. Since energy is conserved in the closed system provided by flyback transformer 56, new secondary currents appear within secondary winding 62 and secondary winding 64 which charge capacitor 70 and capacitor 78, respectively. Secondary winding 62 and secondary winding 64 continue to provide secondary current until there is not enough secondary voltage to forward bias diodes 66 and 76. Diodes 66 and 76 prevent flow of electrical energy stored within capacitors 70 and 78 back into secondary windings 62 and 64, respectively. At precisely the time the secondary current through secondary winding 62 and secondary winding 64 reaches a zero value, control system 52 reinitiates coupling between interface 18 and interface 66 so that primary winding 58 may be recharged.

Control system 52 provides two important functions. First, it couples battery 12 and capacitor 54 to primary winding 58 to charge flyback transformer 56 until the transformer is nearly saturated with magnetic energy. This increases charging efficiency by maximizing the efficiency of flyback transformer 56 by maximizing the magnetic energy storage within flyback transformer 56 without excess battery drainage or excess heating of flyback transformer 56. It is known in the art that if primary winding 56 begins to heat, winding resistance increases and excess circuit power is lost as heat. The second important function of control system 52 is to recouple battery 12 and capacitor 54 to primary winding 58 to begin charging flyback transformer 56 with magnetic energy at precisely the point where the secondary current through secondary windings 62 and 64 reaches zero when diode 66 and 76 are reversed biased. Since at this time the useful magnetic energy in the collapsing magnetic field of flyback transformer 56 has been converted to electrical energy stored in capacitors 70 and 78, and flyback transformer 56 may again be recharged with additional magnetic energy.

To charge capacitors 70 and 78 to the desired voltage, control system 52 successively undergoes cycling by alternately opening the coupling between interface 18 and interface 66 so that power is delivered to the secondary winding during the collapse of the magnetic field, and by closing the coupling to begin the charging cycle at precisely the time that secondary windings 62 and 64 have transferred the stored magnetic energy to capacitors 70 and 78 as electrical energy.

Figure 3:
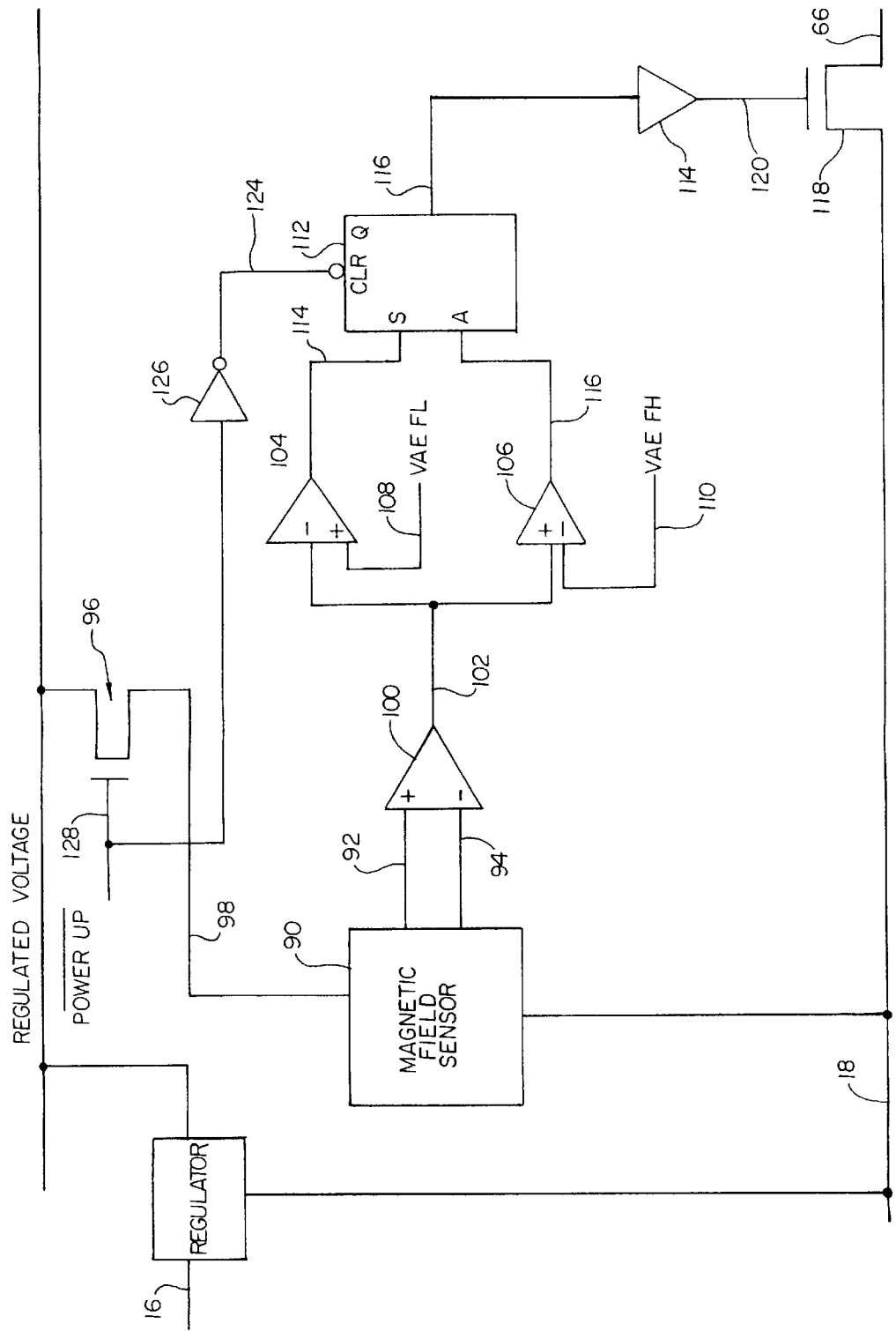
FIG. 3 is a diagram illustrating a preferred embodiment of the present invention.

FIG. 3 is a diagram illustrating a preferred embodiment of the present invention and shows in detail the control system 52 discussed above in FIG. 2. Control system 52 includes a magnetic field sensor 90. Magnetic field sensor 90 in the preferred embodiment is positioned in close proximity to core 60 of flyback transformer 56 to provide a near linear output voltage response between interface 92 and 94 which is proportional to the strength of the magnetic field within flyback transformer 56. Magnetic field sensor 90 is coupled to p-channel MOSFET 96 via interface 98 and to interface 18. Magnetic field sensor 90 provides a voltage output which is nearly linearly proportional to the flyback transformer magnetic field. In a preferred embodiment, magnetic field sensor 90 may be the Giant Magnetoresistive Ratio (GMR) bridge sensor, part number NVS5B5OS, manufactured by Nonvolatile Electronics Inc. (see also, FIG. 5). Magnetic field sensor 90 provides a positive differential voltage output across interface 92 and interface 94 in response to the magnetic field of flyback transformer 92, where the output voltage is positive for either a positive or negative magnetic field from flyback transformer 56. Differential operational amplifier 100 provides a near linear output at interface 102 in response to the positive differential voltage input between interface 92 and interface 94. Differential operational amplifier 100 is coupled to the negative sense input of comparator 104 and the positive sense input of comparator 106 via interface 102. The positive sense input of comparator 104 is coupled to a reference voltage designated VREFL via interface 108. The negative sense input of comparator 106 is coupled to a reference voltage designated VREFH via interface 110. It will be recognized that many alternative embodiments of control system 52 can be implemented in response to the output of sensor 90. For example, the output of interface 92 and 94 could be digitized by a D/A converter and the output feed into a microcontroller or microprocessor. Alternatively, the outputs could be coupled to an integrator and a one-shot timer to generate a representative control signal.

Control system 52 first determines when flyback transformer 56 is nearly saturated with magnetic energy storage and opens the coupling between interfaces 18 and 66, and second, determines when secondary winding 62 and 64 have transferred all useable magnetic energy to capacitors 70 and 78 as stored electrical energy, by sensing the magnetic field from core 60 of flyback transformer 56 at two threshold points. The first threshold point is when flyback transformer 56 is nearly saturated with magnetic energy storage. The second threshold point is when all of the useful magnetic energy has been transferred to capacitors 70 and 78.

The high voltage reference (VREFH) and the low voltage reference (VREFL), are set or calibrated so that comparators 104 and 106 trigger at the first and second threshold points respectively. As magnetic field sensor 90 begins sensing a magnetic field which is increasing in intensity, differential operational amplifier 100 will provides an amplified near linear output voltage response at interface 102. If the output of differential operational amplifier 100 is below VREFL, comparator 104 will see a positive differential between interface 108 and interface 102, and will provide a positive output to the set input of SR flip-flop 112 via interface 114. This is the second threshold point indicating when all of the useful magnetic energy has been transferred to capacitors 70 and 78. If the voltage level on interface 102 is above VREFL, comparator 104 provides a low output on interface 114. If the voltage at interface 102 is above VREFH, comparator 106 provides a high output to the reset input of SR flip-flop 112 via interface 116. This is the first threshold point indicating when flyback transformer 56 is nearly saturated with magnetic energy storage. If the voltage at interface 102 is between VREFL and VREFH, both comparator 104 and 106 provide a low output to SR flip-flop 112.

SR flip-flop 112 is coupled at a Q output to a buffer 114 via interface 116. Buffer 114 drives n-channel MOSFET 118 via interface 120. When SR flip-flop 112 is set, n-channel MOSFET 118 is biased on and electrically couples interface 18 at battery 12 to interface 66 at primary winding 58. This allows battery 12 to begin charging primary winding 58.

SR flip-flop 112 further has a set input at interface 122 and a clear input at interface 124. To initiate charging of primary winding 58 of flyback transformer 56, a set input at interface 122 may be provided to allow SR flip flop 112 to turn on n-channel MOSFET 118 and initiate charging of primary winding 58.

An optional power-down circuit may be provided as shown in FIG. 3 to selectively power up or power down magnetic field sensor 90 and SR flip-flop 112 in order to conserve battery 12. This feature is desirable in battery powered capacitor charging systems. The power down feature is as follows. Magnetic field sensor 90 is coupled to the drain of a p-channel MOSFET 96 via interface 98. The gate of p-channel MOSFET 96 is driven by a "power up" input at interface 128 which is asserted when at a logical low state (e.g. zero volts). Interface 128 couples to inverter 126. Thus, when a "power up" input at interface 128, p-channel MOSFET 96 is turned on and couples interface 16 to magnetic field sensor 90 via interface 98. Furthermore, inverter 126 provides a high output at interface 124 which turns n-channel MOSFET 118 on, thus connecting primary winding 58 with battery 12.

In operation, when flyback transformer 56 is being charged and before it reaches the first threshold point indicating when flyback transformer 56 is nearly saturated with magnetic energy storage, magnetic field sensor 90 provides an output to differential operational amplifier 100 which amplifies the output to a voltage level on interface 102 which is initially between VREFL and VREFH. When the voltage level at interface 102 reaches a value equivalent to VREFH and begins increasing above the value of VREFH, the first reference circuit or comparator 106 provides a first control signal or positive response on interface 116 and resets SR flip-flop 112. When reset, SR flip-flop 112 turns n-channel transistor 118 off, thus disconnecting primary winding 58 at interface 66 from interface 18. This terminates charging of primary winding 58 and allows the magnetic field to collapse and induce secondary currents in secondary winding 62 and secondary winding 64. Once the magnetic field drops to a low enough level where the output of differential operational amplifier 100 drops below VREFL, the second reference circuit or comparator 104 provides a second control signal or positive response to the set input of SR flip-flop 112 through interface 114, thus turning on n-channel MOSFET 118 so that primary winding 58 be recharged.

Figure 4:
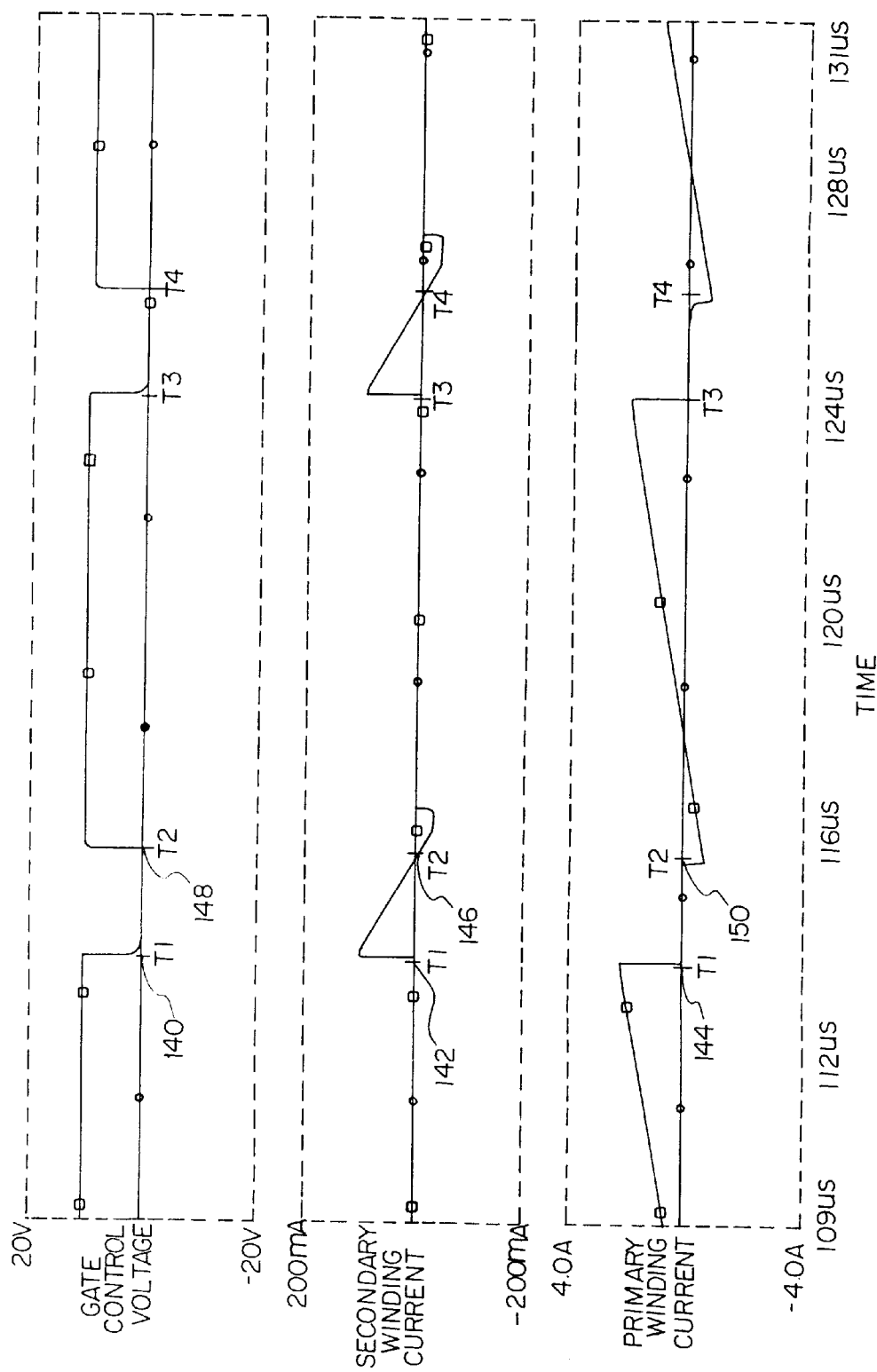
FIG. 4 is a timing diagram illustrating the signal timing relationships in a preferred embodiment of the present invention.

FIG. 4 is a timing diagram illustrating the operation of the control system of FIG. 3. FIG. 4 shows the gain control voltage at interface 120, the secondary winding current flowing between interface 68 and 74, or interface 78 and 82, and the primary winding current flowing between interface 64 and interface 66. Each of the three timing diagrams is graphed against a representative time axis. It is understood that the times which are shown in FIG. 4 are only exemplary in that in any number of preferred embodiments the timing performance may be increased or decreased. The first and second threshold switching points for control system 52 are illustrated. T1 corresponds to the first threshold point or first reference means where the output of differential operational amplifier 100 is increasing in the positive direction as a result of the increasing magnetic field from flyback transformer 56 and is slightly greater than VREFH. T2 corresponds to the second threshold point or second reference means where the output of differential operational amplifier 100 as a result of the decreasing magnetic field and is slightly below VREFL.

It is understood that in the preferred embodiment, the timing performance of control system 52 shown in FIG. 3 is repetitive. That is, T3 corresponds to T1 and T4 corresponds to T2. Control system 52 repeats the performance shown in FIG. 4 until capacitors 70 and 78 are charged to their desired voltage.

In a preferred embodiment, the maximum desired programmable output voltage of capacitors 70 and 78 is 750 volts. Thus, once a start is initiated at interface 122, primary winding 58 begins charging at 109 microseconds as shown in FIG. 4. At the point where flyback transformer 56 has been saturated with magnetic energy, the magnetic field sensor 90 output drives the output of differential operational amplifier 100 to a value above VREFH, thus resetting SR flip-flop 112 and turning off n-channel MOSFET 118, as shown at 140 in the timing diagram for the gate control voltage. Once n-channel MOSFET 118 is no longer turned on, interface 66 of primary winding 58 is no longer coupled to interface 18, and the primary winding currents through primary winding 58 collapse as shown at 144. The collapsing magnetic field induces a secondary winding current as shown at 142, through both secondary winding 62 and secondary winding 64. The secondary winding current continues to flow and convert the magnetic energy to stored electrical energy in capacitors 70 and 78. Once the secondary winding current drops to zero, diodes 66 and 76 are reversed biased and current no longer flows into capacitor 70 or capacitor 78. Just as the secondary winding current flow ceases, as indicated at 146, magnetic field sensor 92 drives the output of differential operational amplifier 100 at interface 102 to a voltage level below VREFL, thus setting SR flip-flop 116 and turning on n-channel transistor 118, as shown at 148 for the gate control voltage. The secondary winding currents shown between T1 and T2, and between T3 and T4, represent when magnetic energy is being stored as electrical energy in capacitor 70 and 78. Therefore, by initiating primary current flow at precisely T2, as shown at 150, the total time required to charge capacitor 70 and capacitor 78 is minimized as there is no undue delay before repeating the charging of primary winding 58. In the preferred embodiment, magnetic field sensor 90 outputs a positive response between interfaces 92 and 94 whether the magnetic field is positive or negative.

Figure 5:
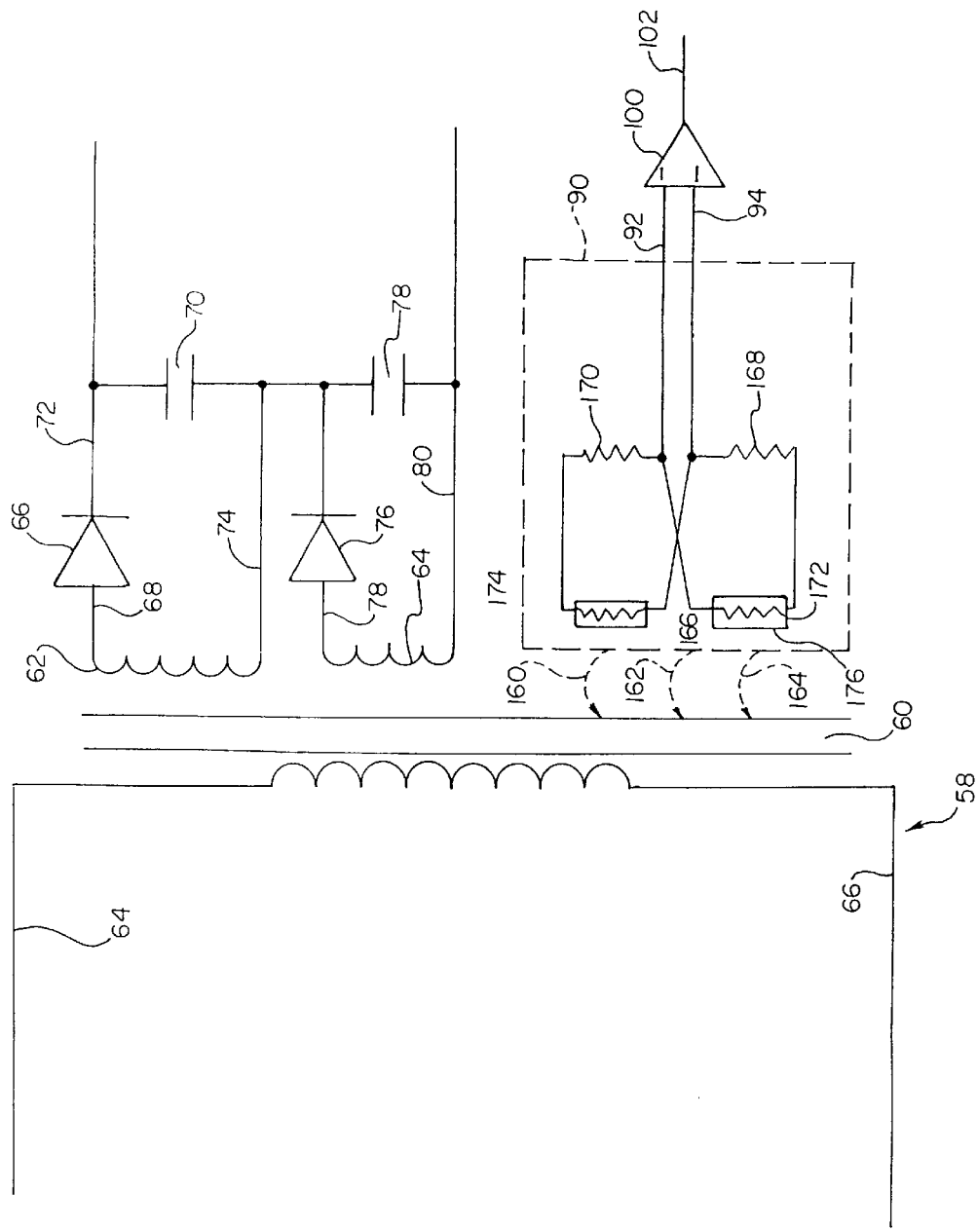
FIG. 5 is a diagram illustrating the magnetic field sensor placement in a preferred embodiment of the present invention.

FIG. 5 is a diagram illustrating the magnetic field sensor 90 placement in a preferred embodiment of the present invention. FIG. 5 shows magnetic field sensor 90 coupling via exemplary field lines 160, 162 and 164 to the magnetic field energy stored in core 60. It is understood that for optimal performance, magnetic field sensor 90 must be placed in close proximity to core 60.

In a preferred embodiment, magnetic field sensor 90 is part number NVS5B50S, manufactured by Nonvolatile Electronics, Inc. It is understood, however, that in other preferred embodiments, any magnetic field sensor providing a response proportional to the magnetic field within core 60 would be within the scope of the present invention.

The resistors are constructed of a plurality of alternating thin film ferromagnetic layers and non-magnetic spacer layers. The resistors have a resistance DR determined by the strength of the magnetic field of the transformer. A reduction in resistance of the resistors in the presence of a magnetic field is due to spin dependence of electron scattering in the ferromagnetic layers. A total amount of resistivity change DR will be dependent upon the strength and positioning of the magnetic field, and the materials and numbers of layers employed.

The bridge is comprised of four resistors indicated at 166, 168, 170 and 172. Resistor 166 has a shield 174 and resistor 172 has a shield 176 to provide shielding against the magnetic field of core 60. Resistors 166 and 172 maintain a constant resistance while flyback transformer 56 is being charged with magnetic energy. Resistors 168 and 170 are not shielded, and thus have a decreasing resistance as the magnetic field is increasing, either in a positive or negative direction. Therefore as the magnetic field coupled from core 60 to magnetic field sensor 90 increases, the voltage level at interface 92 is driven in a positive direction, and the voltage level at interface 94 is driven in a negative direction, resulting in a linear positive differential output voltage from differential operational amplifier 100 at interface 102. This differential output at interface 102 is nearly linear in proportion to the strength of the magnetic field coupled from core 60 to magnetic field sensor 90 as indicated at 160, 162 and 164.

What is claimed is:

1. An field state sensing circuit for use with a flyback transformer having a primary winding, a ferromagnetic core, and at least one secondary winding, the flyback transformer being in a circuit having a current driver coupled to the primary winding and a load coupled to the secondary winding such that the flyback transformer generates a magnetic transformer field in response to a current supplied by the current driver, the field state sensing circuit comprising:

a. a Giant Magnetoresistive Ratio (GMR) bridge arranged in a magnetically cooperative position with the flyback transformer and coupled to the transformer field to thereby change resistance in response to changes in a state of the transformer field occurring in response to operation of the current driver; and b. a control circuit coupled to said GMR bridge and to the current driver, said control circuit providing control signals correlated to the state of the transformer field.

2. A field state sensing circuit as in claim 1 wherein said control circuit includes:

a. a first differential amplifier having first and second input terminals coupled to said GMR bridge and an output terminal providing an electrical signal indicative of the sensed state of the transformer field; and b. a reference comparator circuit coupled to a predetermined reference voltage and to said output terminal, and having a control output terminal to provide said control signals when said electrical signals indicate at least one predetermined state of the transformer field.

3. A field state sensing circuit as in claim 2, wherein said control signals include an activating control signal to activate the current driver when the transformer field is in a first state and a deactivating control signal to deactivate the current driver when the transformer field is in a second state.

4. In an Implantable Cardioverter Defibrillator (ICD) having a battery, a charging circuit coupled to the battery, the charging circuit including a flyback transformer having a primary winding, a ferromagnetic core, and a secondary winding having first and second ends, and a current driver circuit coupled to the battery wherein the flyback transformer causes a magnetic transformer field in response to a state of current flow in the primary winding in response to the current driver circuit, a blocking diode coupled to a first end of the secondary winding, a capacitor coupled to the blocking diode and a second end of the secondary winding, and an output switching circuit coupled across the capacitor, the improvement comprising:

a. sensing means magnetically coupled to the transformer field for continuously sensing a state of the transformer field; and b. control means for controlling the current driver in response to said state of the transformer field.

5. The improvement of claim 4, wherein said sensing means includes:

a. Giant Magnetoresistive Ratio (GMR) means positioned in magnetically cooperative relation to the transformer field for providing varying resistance ratios in response to said state of the transformer field.

6. The improvement of claim 5, wherein said control means includes:
   a. conversion means coupled to said GMR means for converting said varying resistance ratios to corresponding voltage levels; and
   b. reference means coupled to said conversion means for providing control signals based upon said voltage levels to the current driver for controlling the current flow applied to the primary winding.

7. The improvement of claim 5, wherein said control means includes:
   a. differential amplifier means having an output terminal and first and second input terminals coupled to said GMR means for providing voltage levels at said first output terminal, said voltage levels indicative of resistance changes in said GMR means attributable to changes in the transformer field;
   b. first reference means coupled to said output terminal for providing a deactivating signal to the current driving circuit when said voltage level indicates the ferromagnetic core is charged to a predetermined state less than saturation; and
   c. second reference means coupled to said output terminal for providing an activating signal to the current driving circuit when said voltage level indicates that the ferromagnetic core is optimized for another application of current to the primary winding.

8. A charging circuit for charging a high voltage capacitor system from a low voltage battery, the charging circuit comprising:
   a. a flyback transformer having a primary winding, a ferromagnetic core, and at least one secondary winding;
   b. a current driver circuit coupled to said primary winding, said current driver circuit having an input terminal for coupling to the battery and a control terminal, said current driver circuit providing current flow in response to first control signals supplied to said control terminal and substantially stopping current flow in response to second control signals applied to said control terminal;
   c. a giant magneto resistive ratio (GMR) bridge device positioned in a magnetically coupled cooperative relation to said flyback transformer, said GMR bridge device having GMR terminals, and said GMR bridge providing varying resistance ratios in response to a state of the magnetic fields of said flyback transformer as coupled to said GMR bridge;
   d. a conversion circuit coupled to said GMR terminals and having a conversion terminal to provide signal levels indicative of said varying resistance ratios;
   e. a first reference circuit coupled to said conversion terminal, and having a first control terminal coupled to said input terminal of said current driver circuit to provide said first control signals when said signal levels indicate said ferromagnetic core is charged to a first predetermined state approaching, but less than, saturation; and
   f. a second reference circuit coupled to said conversion terminal, and having a second control terminal coupled to said input terminal of said current driver circuit to provide said second control signal when said signal levels indicate said ferromagnetic core has recovered to a second predetermined state less than said first predetermined state and optimized for a subsequent application of current to the primary winding to utilize the residual field of said transformer during a charging cycle.

9. An apparatus for controlling the current to a primary winding of a flyback transformer in a capacitor charging circuit powered by a battery, the flyback transformer producing a magnetic field, the apparatus comprising:
   a. a magnetic field sensor coupled in close proximity to the flyback transformer for providing a differential voltage output response which is directly proportional to the strength of the magnetic field;
   b. a differential operational amplifier coupled to the magnetic field sensor for providing a substantially linear output in response to the differential voltage input;
   c. a first comparator having a first and second input, the first input coupled to the differential operational amplifier, the second input being coupled to a high voltage reference level, the first comparator providing a first output when the substantially linear output is greater than the high voltage reference level;
   d. a second comparator having a first and second input, the first input coupled to the differential operational amplifier, the second input being coupled to a low voltage reference level, the second comparator providing a second output when the substantially linear output is lower than the low voltage reference level;
   e. a flip-flop circuit having a reset input coupled to an output of the first comparator, a set input coupled to the output of the second comparator, and an output; and
   f. a switch for controlling power to the primary winding of the flyback transformer, the switch having a control input coupled to the output of the flip-flop circuit, a first terminal of the switch coupled to the primary winding, a second terminal of the switch coupled to the battery, the switch decoupling the first terminal from the second terminal when a first threshold is sensed by the magnetic field sensor indicating that the flyback transformer is nearly saturated with magnetic energy storage and the first comparator provides the first output, the first terminal being coupled to the second terminal when a second threshold is sensed by the magnetic field sensor indicating that substantially all the magnetic energy stored in the flyback transformer has been transferred to the capacitor and the second comparator provides the second output.

10. In a capacitor charging circuit having a current driver circuit, a flyback transformer including a primary winding, a ferromagnetic core, and at least one secondary winding and providing a magnetic transformer field when the current driver circuit applies or removes current flow in the primary winding, a blocking diode and a capacitor coupled across the secondary winding, a method of optimizing operation of the circuit to charge the capacitor comprising the steps of:
   a. positioning a giant magneto resistive ratio (GMR) device in a magnetically cooperative position relative to the flyback transformer;
   b. continuously sensing a state of the transformer field using the GMR device;
   c. converting the sensed state of the transformer field to second control signals when the field has a second predetermined state and to first control signals when the field has a first predetermined state;
   d. enabling operation of the current driver circuit in response to said second control signals;

e. disabling operation of the current driver circuit in response to said first control signal; and f. repeating steps b-e until the capacitor has been charged to a predetermined voltage level.

11. The method of claim 8, wherein said first predetermined state is near to but less than saturation of the ferromagnetic core.

12. The method of claim 9, wherein said second predetermined state is selected at a field strength occurring after the field has collapsed to a level near zero.

13. An Implantable Cardioverter Defibrillator (ICD) comprising:

a biocompatible housing having positioned therein a low voltage battery, a high voltage output switching system, and a high voltage charging system operably coupled therebetween, the high voltage charging system including:

a flyback transformer having a primary winding operably coupled to said battery, a ferromagnetic core, and at least one secondary winding;

a high voltage capacitor system operably coupled between said at least one secondary winding and said output switching system;

a magnetic sensor arranged in a magnetically cooperative position with said flyback transformer and operably coupled to a magnetic field generated by said flyback transformer; and a control circuit operably coupled to said magnetic sensor and operably coupled between said battery and said primary winding, said control circuit providing power to said primary winding as a function of the state of the magnetic field as detected by said magnetic sensor.

14. The ICD of claim 13 wherein the magnetic sensor is a giant magneto resistive ratio (GMR) bridge device.

15. The ICD of claim 13 further comprising power down circuitry operably coupled to said magnetic sensor and to said control circuit to minimize power drain from said battery during periods in which said capacitor system is not being charged.

\* \* \* \* \*